United States Patent [19]

Lopez

[11] Patent Number: 5,361,507
[45] Date of Patent: Nov. 8, 1994

[54] INFANT MEASURING DEVICE WITH PROGRESS CHARTING CAPABILITY

[76] Inventor: Claudio I. Lopez, 10157 Cedar Dune Dr., Tampa, Fla. 33824

[21] Appl. No.: 55,279

[22] Filed: May 3, 1993

[51] Int. Cl.$^5$ ............................................. A61B 5/107
[52] U.S. Cl. ........................................ 33/515; 33/512; 33/811; 33/812
[58] Field of Search ............... 33/511, 512, 515, 806, 33/810, 811, 812, 712, 3 R, 3 A, 485, 563, 566, 474, 573

[56] References Cited

U.S. PATENT DOCUMENTS

| | | | |
|---|---|---|---|
| 1,555,792 | 9/1925 | Souder | 33/810 |
| 2,096,551 | 10/1937 | Johnson | 33/3 A |
| 3,020,643 | 2/1962 | Moran | 33/512 |
| 3,376,650 | 4/1968 | Cook | 33/566 |
| 3,438,134 | 4/1969 | Schunk | 33/515 |
| 4,911,175 | 3/1990 | Shizgal | 128/774 |
| 4,930,221 | 6/1990 | Taylor | 33/811 |
| 4,939,849 | 7/1990 | Johnson | 33/512 |

*Primary Examiner*—Alvin Wirthlin

[57] ABSTRACT

An infant measuring and growth charting device having a substantially flat bottom base of a length and width to accommodate infants to be measured, a fixed head board, and a slideable locking foot board, the infant being place in the device, the foot board slid forward to touch the bottoms of the infants feet, the infants legs being fully extended, and the device locked into place. An embedded ruler is affixed into the upper surface of the bottom base, and a viewing hole in a portion of the sliding foot board, over the embedded ruler, follows, and displays the measurements of the infant, and when the exact measurement of the infant is displayed in the viewing hole, the foot board is locked into that position, and this exact measurement will be in the viewing hole for later recording, or, photographing. After the infant is removed from the measuring device, a T-square charting device is inserted into the same groove used to guide the moveable foot board. This charting device allows the user to insert a standard growth chart onto the device, align pertinent data values on the standard growth chart, with guide lines on a transparent cursor plate on the T-square, and holes being provided at the intersections of these guide lines allow a pencil, or pen, or marking device, to be inserted through the cursor plate, and onto the chart, to mark, and plot the several parameters involved in the growth of the infant in a very precise manner.

1 Claim, 4 Drawing Sheets

INFANT MEASURING DEVICE WITH PROGRESS CHARTING CAPABILITY

BACKGROUND OF INVENTION

This invention relates to an apparatus and method of measuring the height, or, length, of an infant, and, charting the growth, head circumference, weight, and other parameters associated with the child. It provides a safe, and reliable method of measuring the length of the infant, while simultaneously providing a locking mechanism to hold this exact measurement of the infant in a viewable location, to be stored on the device until the attendant can conveniently record the height on a permanent chart for the infant.

As an additional feature of this device, (and this is an improvement over the prior art of this inventor, submitted on patent application Ser. No. 07/959,340, filed on Oct. 13, 1992 now abandoned), a charting mechanism is provided for accepting a standard infant progress chart onto the invention, locating the progress coordinates and marking the appropriate progress points on the standard progress chart, for permanent progress charting for the infant.

It has been customary for health care professionals to manually hold the infant, and measure the length by placing the infant on an examining table, and gently stretching out the child's legs, while attempting to make the measurement, using a flexible tape measure, or, a wooden ruler of sorts. Sometimes a pencil is used to make a pencil mark at the head, and the feet of the infant, on the paper on the examination table, and, when the infant is removed, and placed in a safe place, the distance between the pencil marks is measured, and recorded. There are many problems associated with these types of measuring systems, which can translate into misreadings of the infants progress.

Another approach to the height measurement of infants is to place the infant on the examination table, gently stretch the infants legs to an extended position, and use a tape measure to try to get a measurement, memorize the measurement, remove the infant from the table, and place it in a safe place, and then record the measurement. There are several problems with this type of measuring. The measurement is not accurate, or, the person making the measurement forgets the measurement, or translates it wrong. Also, it normally requires at least two persons to make the measurement.

In U.S. Pat. No. 4,197,649, Flinn teaches a ruled straight edge, having transparent properties, and provided with a surface gripping strip of material, and a marking implement groove. Such a device is useful for scanning and underlining books, letters, and other flat documents, and could be used to measure an infant. However, it would be inconvenient for measuring these infants, because the device is designed to be placed on top of a flat surface for measuring. Also, the magnification, surface gripping, and marking capabilities are not useful in the measuring of infants. Further, there are no facilities for measuring head circumference, and weight.

Still another approach to the problem of measuring the height of infants is taught in the art of Bergstedt, in U.S. Pat. Des. No. 277,939, wherein a child's growth and height measurement is continually recorded, as the child grows. The invention is intended to be hung on the wall, with the child standing in front of the device, while a second person records the height measurement. This teaching is clearly unsuitable fro use with infants, who are not capable of standing,. If the device were used horizontally, with the infant laid prone, measurement would be haphazard, and again, would require memorization of the height for later recording, or, it would require the services of at least two persons. Also, the ornamental deer's head, being made from a rigid material, could possibly cause injuries to infants. Further, there are no facilities on the device to measure and chart the head circumference, nor the weight of the infant.

SUMMARY OF THE INVENTION

Accordingly, it is an object of this invention to provide a new, and improved method and apparatus for measuring the exact length of an infant, and locking the device at that measurement for later recording of the height of the infant, or, for later photographs of the measurement.

Another object of this invention is to provide this device for measuring an infant in a safe, hands-on method, requiring only one attendant for the entire measuring session, and having the infant under control at all times in a safe manner.

Another object of this invention is to provide this apparatus with a clean paper covering of the device for each infants measurement.

Still another object of this invention is to provide this apparatus with an accurate, and more reliable measurement than is taught in the prior arts, by having the infant under control at all times.

Yet another object of this invention is to provide this apparatus with provision to accurately measure the infant, and, to lock this measurement in a viewing window, for later recording, as opposed to having to memorize the measurement for later recording.

Still another object of this invention is to provide this apparatus with a charting device, as a part of the measuring device apparatus, in order that a standard infant progress chart can be updated accurately and easily, thereby allowing for easy charting of the progress of the infant, for height, weight, and head circumference, and other parameters.

In carrying out this invention in the illustrative embodiment thereof, a measuring device is provided, having a substantially flat lengthwise base, and two measuring end pieces, one end piece being a non-moveable perpendicular headboard, affixed to the flat base, and the other end piece being a slideable perpendicular foot board, and the foot board being slideable lengthwise the flat base, using a formed groove in the flat lengthwise base, and the foot board having a locking arrangement into the formed groove in the flat base, thereby holding the foot board in the measured location of the infant, for later recording of the measurement.

Now, a standard length of ruler material is embedded lengthwise into the flat base, alongside the lengthwise formed groove in the flat base, and, as the foot board is slid from one position to another, to conform to the length of the infant, the exact length of the infant appears in the viewing hole in the locking portion of the foot board.

A roll of sanitary paper is attached onto the head board, and this sanitary paper is fed through a spring loaded slot at the top of the head board, and is pulled through the slot to cover the top of the flat base, where the infant is to be laid for measurement, the paper being restrained from sliding sideways, or other wise, by restraining material at the headboard, and the footboard, this restraining material being of a bungee, or velcro type material stretching across the lateral dimension of the flat base, at the headboard, and at the footboard.

The first step in the measuring process is to unroll a supply of paper to cover the flat base, and secure the paper by using the restraining material, creating a firm, sanitary space for the infant. Now, the foot board is unlocked, and moved a sufficient distance from the head board, and a n infant is placed in the opening between the head board, and the footboard, with the infant's head touching the headboard, and resting on a provided head pad. The infant's legs are then gently straightened, and the foot board is slid, or moved to a forward position to touch the infants heels, with the legs fully extended. The foot board is then locked in this location, the actual length of the infant appearing in the hole in the foot board, above the ruler, and displaying the actual length of the infant. The footboard is then locked in this location, thereby holding the footboard in this location, with the infant's length still being displayed in the hole in the footboard, for later recording. The infant is then removed from the measuring device, for other measurements of the infant, which are to be plotted, using the measuring device, to form the entire infant's progress chart.

It should be noted that only one person is required to perform the entire measuring routine, and, that the position of the headboard, and the footboard has been reversed from their positions in the prior art of the inventor, for easier and safer handling, and manipulation of the infant in the device.

This invention also includes a device to aid the attendant in accurately charting the infant's length, and other data that is to be plotted on a standard growth chart, of the type recommended by the U.S. Public Health Service, and routinely kept by pediatricians. This charting, and plotting device consists of a slideable, removeable, T-square device, having the lengthwise extension of the T-square sized to fit into a formed transverse groove, which extends lengthwise of the flat base of the measuring device, and a transparent cursor plate, supplied with vertical and horizontal guide lines, and appropriate holes, through which the data may be plotted onto the growth chart in an accurate manner.

A positioning block is fitted onto the T-square handle, and transverse groove, to hold the T-square device in position, and to provide a surface for aligning the growth progress form on which the data will be plotted. The positioning block has a deep central groove through which the T-square handle may pass, as well as a wider, shallower groove to allow free movement of the cursor plate.

Conveniently, the attendant may place a standard growth chart on the base of the invention, under the T-square, so that its bottom edge is flat against the edge of the positioning block. The attendant now moves the growth chart laterally on the base board, and under the T-square, so that the infants age is under one of the two vertical guide lines. The T-square device is then moved transversely until the infants length measurement is under the horizontal guide line. At the intersections of the vertical and horizontal guide lines, holes are present in the cursor plate. These holes allow the attendant to insert a pencil, or, pen, thus conveniently and accurately recording the infants length measurement on the growth chart, at the point exactly corresponding to the infants age.

This charting device may also be used to precisely plot other data, for example, the infants weight, head circumference, and length-to-weight ratio. When the charting device is not in use, it can be removed, thus allowing more travel for the foot board, so that larger infants can be measured.

Conveniently, the user may use this measuring device to measure the exact height of an infant, having the infant always in control, lock in the height in the viewing circle of the device, and record the height later, and, also, place a progress chart on the device, and using the T-square and cursor plate, record the weight, head circumference, and other parameters on a standard progress chart, in an exact manner, and, only one person is required to perform all of these functions.

BRIEF DESCRIPTION OF THE DRAWINGS

This invention, together with other objects, features, aspects and advantages thereof, will be more clearly understood from the following description, considered in conjunction with the accompanying drawings.

Four sheets of drawings are furnished. Sheet 1 contains FIG. 1, and 2. Sheet 2 contains FIGS. 3, 4, and 5. Sheet 3 contains FIGS. 6, and 7, and sheet 4 contains FIG. 8.

DESCRIPTION OF THE PREFERRED EMBODIMENTS

Figure 1:
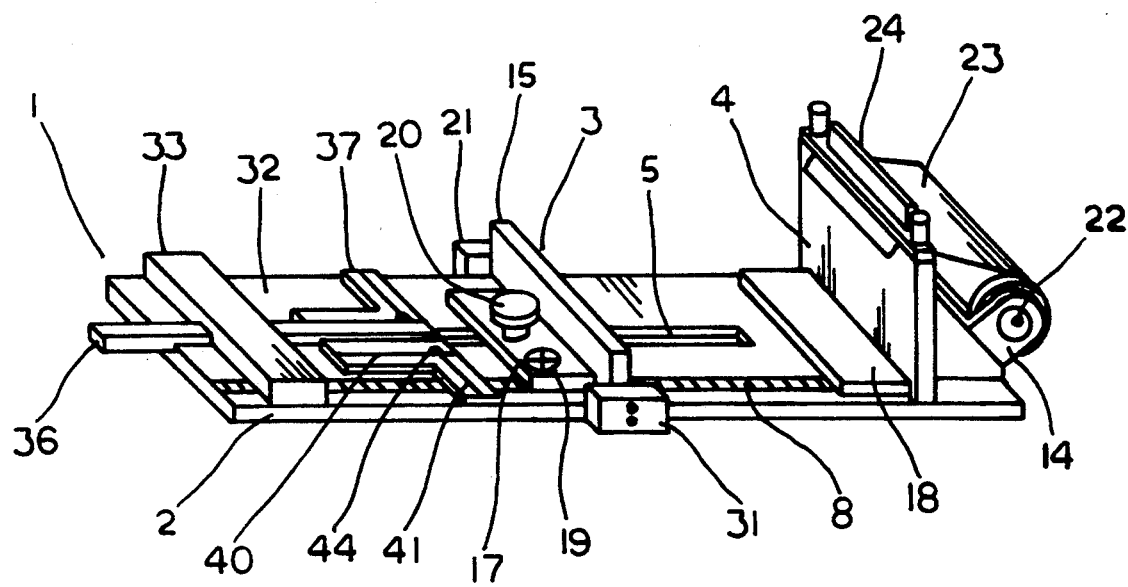
FIG. 1 is an isometric representation of the apparatus, showing the preferred embodiment.

Referring now to FIG. 1, an infant measuring device, referred to generally by the reference numeral 1 is made of a suitable material, and comprises a flat horizontal bottom base 2 of a suitable width to hold an ordinary infant, a fixed head board 4, and a moveable foot board 3. Horizontal base 2 has a "T" shaped groove 5 cut into its upper surface, and the groove 5 extends approximately three quarters of the length of base 2, and a T-square charting device 32 slides in the T shaped groove 5, and is captured therein, and is held in position by positioning block 33.

Now, moveable foot board 3 has an upright 15, a rearward perpendicular supporting section 17, and two side travel guides 21, and 31. Rearward supporting section 17 has a viewing hole 19 of a suitable diameter for viewing, drilled through its surface, and is locked in position by locking mechanism 20.

Head board 4 has paper roll holding frame 14 affixed thereto, and holding frame 14 having a roll of sanitary paper 23, supported on paper holder spindle 22, and sanitary paper 23 feeding onto base 2 through spring loaded paper hold-down device 24.

Figure 2:
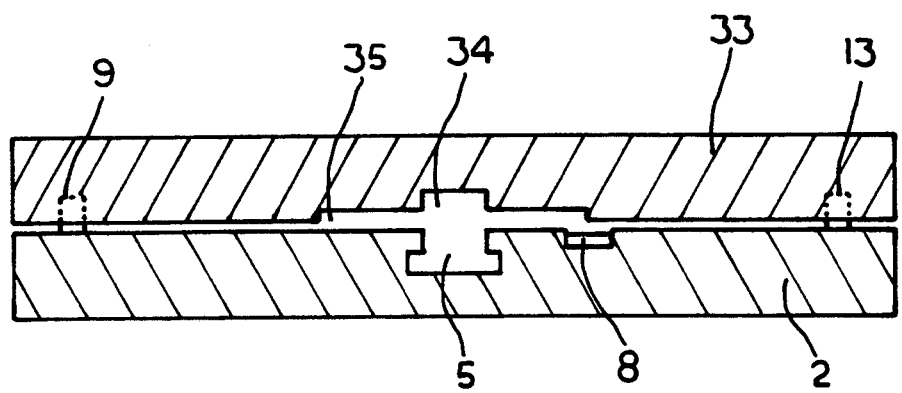
FIG. 2 is an elevation view of the front of the base, showing the formed groove, the positioning block, and the end travel stops.

Referring now to FIG. 2, we see the end of base 2 having a "T" shaped groove 5 cut into its top surface, and extending a distance lengthwise along base 2 for approximately three quarters the length of base 2, and two blocking studs 9, and 13 extending upwards from the surface of base 2, and into holes in the underside of positioning block 33, and ruler 8, ruler 8 being embedded flush into upper surface of base 2. Now, positioning block 33 has a deep central groove 34 to allow the passage of handle 36 of T-square charting device 32, which can be seen more clearly in FIG. 1. Positioning block 33 also has a wide, shallow groove 35 through which cursor plate 37 can be moved in the transverse direction.

Figure 3:
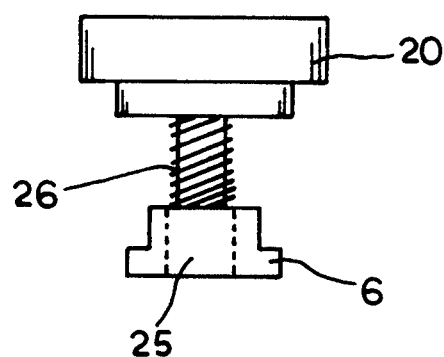
FIG. 3 is a front view of the locking arrangement for the foot board.

Referring now to FIG. 3, we see locking "T" block 6 having threaded receptacle 25, and locking knob 20, with matching threaded rod 26 inserted into receptacle 25.

Figure 4:
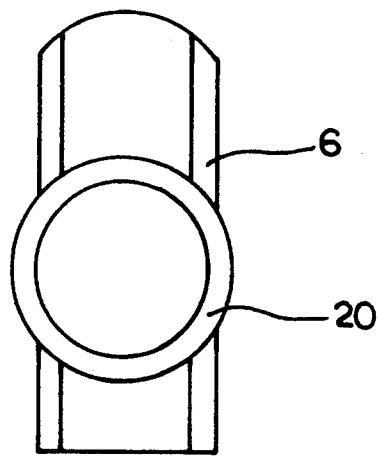
FIG. 4 is a top view of the locking arrangement for the foot board, and locking in the height of the infant in the viewing circle.
Figure 5:
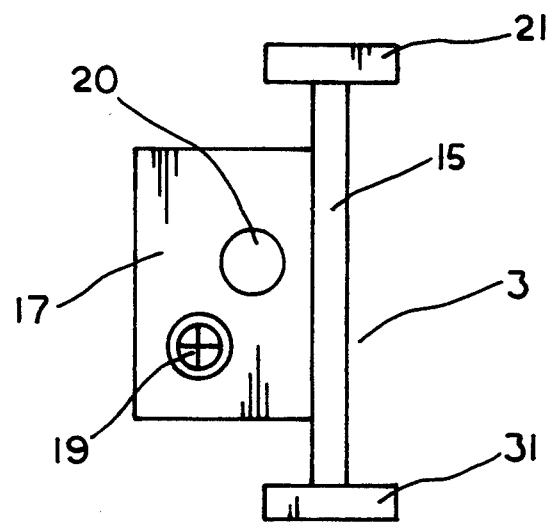
FIG. 5 is a top view of the foot board, the locking arrangement, the viewing hole, and the side guide blocks.

Progressing now to FIG. 4 we see a top view of locking knob 20, inserted into locking "T" block 6. Moving on to FIG. 5 we see a top view of moveable foot board 3, rearward perpendicular supporting section 17 having viewing hole 19 and locking knob 20, and upright 15 attaching two guide blocks 21, and 31.

Figure 6:
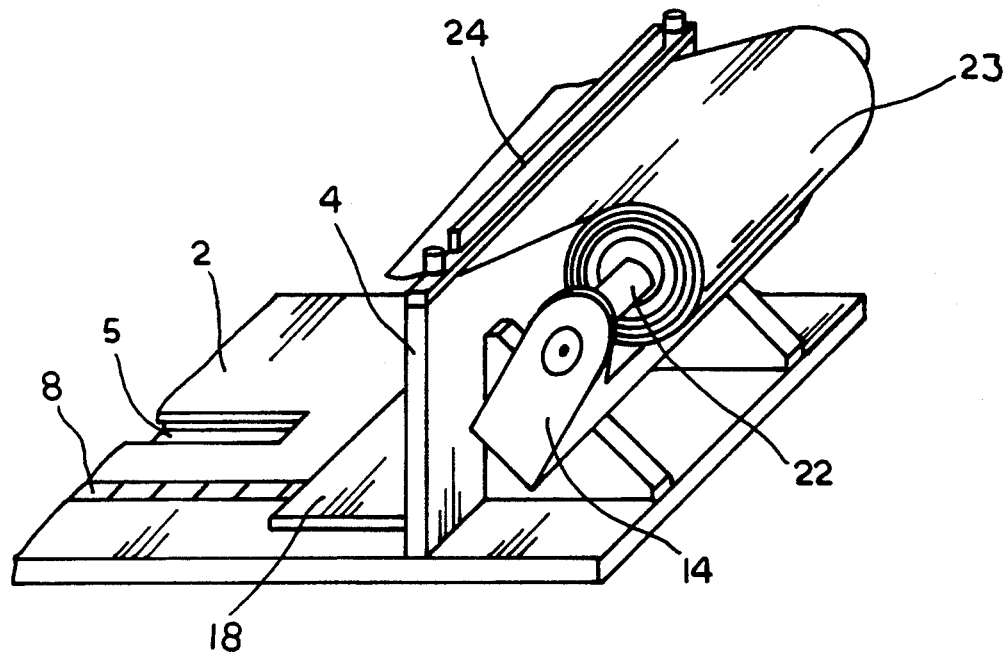
FIG. 6 is an isometric view of the paper roll, together with the paper holder frame, and spindle, the spring loaded slot at the top of the head board, and the comfort pad.

In FIG. 6 we see head board 4 attached onto base 2, and having paper roll holding frame 14, and frame 14 having a roll of sanitary paper 23 being dispensed through spring loaded paper hold down device 24. Sanitary paper roll 23 is supported in dispensing position by paper holder spindle 22. Comfort pad 18 is also affixed onto upper surface of base 2, immediately in front of head board 4, so that the head of the infant to be measured may be comfortably rested on pad 18 during measurement procedure.

Figure 7:
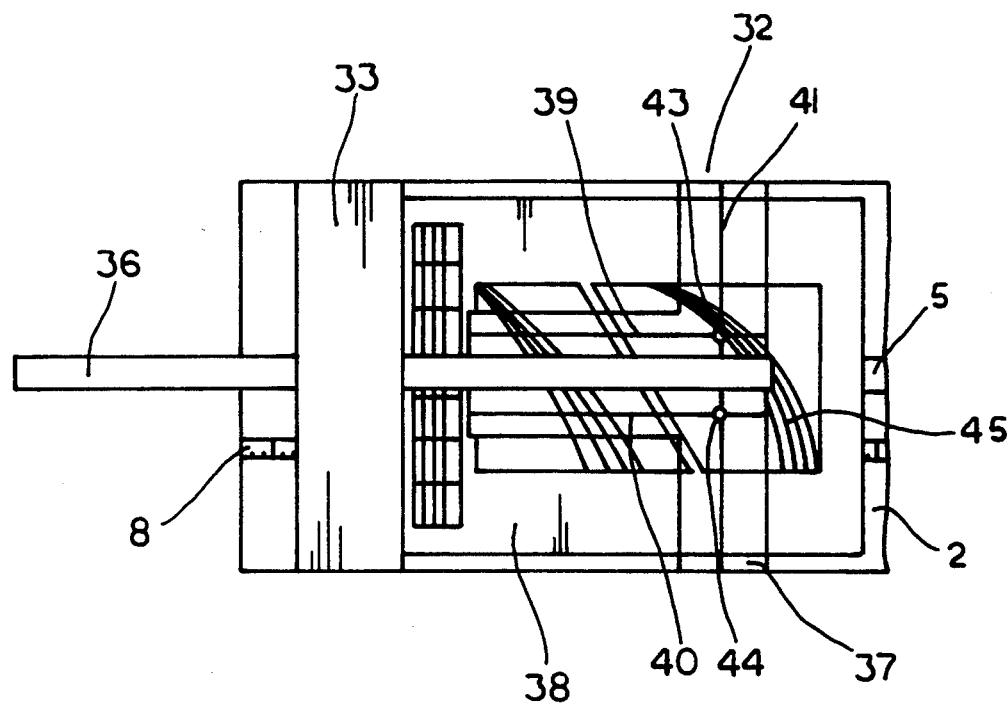
FIG. 7 is a top view of the charting device, showing the T-square, the positioning block, and a typical growth chart.

Moving on to FIG. 7, we see a top view of the opposite end of base 2, having T-square charting device 32 inserted into transverse groove 5, and positioning block 33 installed over charting device 32 and groove 5, the location of block 33 being established by blocking studs 9, and 13, over which block 33 is installed Now, to plot the infants length measurement, the user places a standard growth chart 39 on top of base board 2, and positions its bottom edge firmly against positioning block 33. The user now moves growth chart 38 in the lateral direction, so that the infants age in months is aligned with one of the two vertical guide lines 39, and 40, inscribed on cursor plate 37. Now, charting device 32 is moved in the transverse direction until the infants current length is located under horizontal guide line 41, inscribed on cursor plate 37, handle 36 being provided with a transverse slot 42, (shown more clearly in FIG. 8), so that growth chart 38 will not be pushed out of position by the transverse movement of charting device 32.

Now, with the infants age aligned to guide line 39, or 40, and the infants length aligned to guide line 41, one of the two plotting holes 43, or 44 will be located at the correct point on growth curves 45, for plotting the current measurement. Other measurement data, and parameters on the growth chart, including head circumference, and weight, may also be charted by using device 32 and chart 38 in a similar manner for these measurements.

Now, charting device 32 and positioning block 33 can be removed when no charting is being done, or, when more travel of foot board 3 is required for the measurement of longer infants. When block 33 is removed, blocking studs 9, and 13 (shown in FIG. 2) serve as travel limiting devices for foot board 3.

Figure 8:
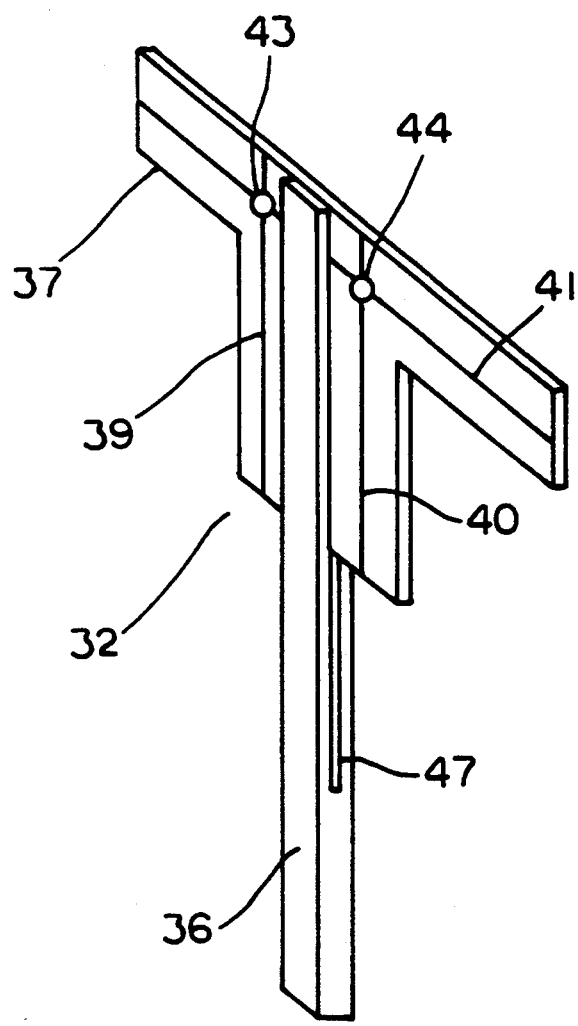
FIG. 8 is an isometric view of the T-square, showing the handle, the cursor plate, the guide lines, and the marking holes.

Referring now to FIG. 8 we see a view of T-square charting device 32, clearly showing handle 36 having transverse slot 42, and transparent cursor plate 37, having vertical guide lines 39, and 40, horizontal guide line 41, and plotting holes 43, and 44.

Accordingly, a very unique, attractive, and convenient method and apparatus are provided for measuring an infant in a safe, hands-on method, having the measurement recorded in a viewing hole for later recording in the records, and also for plotting the associated growth parameters on a standard growth chart, or other individual charting methods, in a neat and accurate manner.

Since minor changes and modifications varied to fit particular operating requirements and environments will be understood by those skilled in the art, the invention is not considered limited to the specific examples chosen for purposes of illustration, and includes all changes and modifications which do not constitute a departure from the true spirit and scope of this invention as claimed in the following claims and reasonable equivalents to the claimed elements.

What is claimed is:

1. An infant measuring, and charting device, comprising:

a bottom base, said bottom base being a substantially flat, elongated piece of material, said bottom base having first and second ends, a bottom surface, and a top surface, said bottom base having a length between said first and second ends and a width sufficient to accommodate an infant for recording the infant's length, said bottom base having a ruler inlaid along the length of said top surface, said bottom base having an inverted T-shaped groove formed centrally along said top surface, said groove extending a distance from the first end of said bottom base and terminating before reaching said second end of said bottom base, a head board affixed onto said bottom base, and located at said second end of said base, and extending perpendicular upward a distance from said bottom base, said head board having a spring loaded paper holding means affixed at its upper end, a head comfort pad affixed to said bottom base, said head comfort pad being located on one side of said head board, and adjacent thereto, a foot board, said foot board being substantially L-shaped having an upward extending vertical portion, and a substantially flat horizontal portion, said foot board being slidably affixed onto said bottom base, said foot board having locking means attached thereto, said locking means including a T-shaped block inserted into said inverted T-shaped groove and a locking screw extending through said horizontal portion into said block, said foot board having two guide rails affixed thereto, said guide rails being affixed to opposite sides of said foot board for engaging said bottom base, said foot board including viewing means for viewing said inlaid ruler, said viewing means being a substantially circular hole in said horizontal portion and located over said ruler, said ruler being affixed to said bottom base in a position to present an exact reading of an infant's height in said hole, said bottom base having a paper holder frame affixed thereto, said frame including a removable spindle, said spindle providing means for unrolling said paper, said paper being inserted between the upper end of said head board and said spring loaded paper holding means, thereby forming a sanitary paper covering for said bottom base, said bottom base having means for charting an infant's measurements onto a standard growth chart to be located on said base, said charting means including a T-square, said T-square having an elongated portion for insertion into said T-shaped groove in said bottom base, said T-square further having a viewing cursor plate affixed at one end of said T-square, said cursor plate having at least two marking holes extending through its surface, said marking holes being located strategically to allow charting on said growth chart in at least two positions of said growth chart, said bottom base also having retaining means for retaining said charting means on said bottom base.

* * * * *